United States Patent [19]

Ebling et al.

[11] Patent Number: 5,207,673

[45] Date of Patent: May 4, 1993

[54] FIBER OPTIC APPARATUS FOR USE WITH MEDICAL LASERS

[75] Inventors: Wendell V. Ebling, El Toro; John F. Forkner, South Laguna; Robert J. Freiberg, Mission Viejo; Robert E. Woodard, El Toro, all of Calif.

[73] Assignee: Premier Laser Systems, Inc., Irvine, Calif.

[21] Appl. No.: 803,919

[22] Filed: Dec. 6, 1991

Related U.S. Application Data

[63] Continuation of Ser. No. 364,703, Jun. 9, 1989, abandoned.

[51] Int. Cl.$^5$ ............................................. A61N 5/06
[52] U.S. Cl. ..................................... 606/16; 606/15; 606/17; 129/397; 129/398; 385/33; 385/38
[58] Field of Search ........................ 128/395, 392, 398; 606/2-19; 385/33-35, 38

[56] References Cited

U.S. PATENT DOCUMENTS 3,304,403  2/1967  Harper .

(List continued on next page.)

FOREIGN PATENT DOCUMENTS

| 069351 | 1/1983 | European Pat. Off. . |
| 105706 | 4/1984 | European Pat. Off. . |
| 0206331 | 12/1986 | European Pat. Off. . |
| 0206332 | 12/1986 | European Pat. Off. . |
| 0248520 | 12/1987 | European Pat. Off. . |
| 0255974 | 2/1988 | European Pat. Off. . |
| 0281161 | 9/1988 | European Pat. Off. . |
| 2828322 | 1/1980 | Fed. Rep. of Germany . |
| 3225452 | 1/1983 | Fed. Rep. of Germany . |
| 3719561 | 1/1988 | Fed. Rep. of Germany . |
| 258360A | 7/1988 | Fed. Rep. of Germany . |
| 2513109 | 9/1981 | France . |
| 163307 | 7/1988 | Japan . |
| 2023004 | 12/1979 | United Kingdom . |

OTHER PUBLICATIONS

Righini et al., "Le Fibre Ottiche i Medicina", Alta Frequenza, vol. 47, No. 3, 1978, pp. 165-171 (with copy of English language translation).

Sydney A. Self, "Focusing of Spherical Gaussian Beams", Applied Optics, vol. 22, No. 5, Mar. 1, 1983.

Allison et al., "Use of Fiber Optics for Remote UF$_6$ Laser-Induced Fluorescent Measurements", Proceedings of SPIE, vol. 380, Apr. 11-15, 1983, pp. 369-375.

(List continued on next page.)

Primary Examiner—David M. Shay
Attorney, Agent, or Firm—Knobbe, Martens, Olson & Bear

[57] ABSTRACT

An optical apparatus functions as a laser catheter for removal, penetration or treatment of human tissue or other biotic material. The arrangement of the optical components, including the focal length of the lens and the spacing between the lens and the source of light is selected to yield an output beam having advantageous characteristics which are particularly suitable for medical laser treatment. Such characteristics include a relatively long beam throw, a long focal range, and a small output beam waist. A hollow tip, preferably conical in shape, is utilized to provide a tactile indicator as to the cutting action of the output beam.

58 Claims, 4 Drawing Sheets

U.S. PATENT DOCUMENTS

| | | | |
|---|---|---|---|
| 3,622,743 | 11/1971 | Muncheryan | 606/16 |
| 3,693,623 | 9/1972 | Harte et al. | |
| 3,809,072 | 5/1974 | Ersek et al. | |
| 3,821,510 | 6/1974 | Munchenyan | 128/395 |
| 3,843,865 | 10/1974 | Nath | 128/395 |
| 3,865,113 | 2/1975 | Sharon et al. | 606/19 |
| 4,185,633 | 1/1980 | Prozorov et al. | |
| 4,207,874 | 6/1980 | Choy | 128/398 |
| 4,266,549 | 5/1981 | Kimura | 128/395 |
| 4,270,845 | 6/1981 | Takizawa et al. | 606/19 |
| 4,273,109 | 6/1981 | Enderby | |
| 4,273,127 | 6/1981 | Auth et al. | |
| 4,281,931 | 8/1981 | Chikama | |
| 4,398,790 | 8/1983 | Righini et al. | 350/96.18 |
| 4,418,688 | 12/1983 | Loeb | 128/398 |
| 4,421,382 | 12/1983 | Doi et al. | 606/15 |
| 4,458,683 | 7/1984 | Saito et al. | 128/395 |
| 4,487,206 | 12/1984 | Aagard | |
| 4,517,974 | 5/1985 | Tanner | |
| 4,519,390 | 5/1985 | Horne | |
| 4,521,070 | 6/1985 | Sottini et al. | |
| 4,537,193 | 8/1985 | Tanner | 606/19 |
| 4,538,609 | 9/1985 | Takenaka et al. | 128/395 |
| 4,559,442 | 12/1985 | Eisenberg | 606/6 |
| 4,564,011 | 1/1986 | Goldman | 128/398 |
| 4,592,353 | 6/1986 | Daikuzono | |
| 4,601,548 | 7/1986 | Nishikawa | 350/96.26 |
| 4,611,288 | 9/1986 | Duret et al. | |
| 4,641,912 | 2/1987 | Goldenberg | |
| 4,657,014 | 4/1987 | Edelman et al. | |
| 4,671,273 | 6/1987 | Lindsey | 128/398 |
| 4,678,268 | 7/1987 | Russo et al. | 350/96.18 |
| 4,686,979 | 8/1987 | Gruen et al. | |
| 4,693,244 | 9/1987 | Daikuzono | |
| 4,694,828 | 9/1987 | Eichenbaum | |
| 4,732,448 | 3/1988 | Goldenberg | |
| 4,736,743 | 8/1988 | Daikuzono | |
| 4,761,054 | 8/1988 | Ishimori et al. | 350/96.26 |
| 4,772,093 | 9/1988 | Abele et al. | |
| 4,773,899 | 9/1988 | Spears | 606/7 |
| 4,778,247 | 10/1988 | Carpenter | |
| 4,784,132 | 11/1988 | Fox et al. | |
| 4,784,135 | 11/1988 | Blum et al. | |
| 4,807,987 | 2/1989 | Bastable et al. | |
| 4,865,029 | 9/1989 | Pankratov et al. | 606/17 |

OTHER PUBLICATIONS

Grundfest et al., "Laser Ablation of Human Athersclerothic Plaque Without Adjacent Tissue Injury", Journal of the American College of Cardiology, vol. 5, pp. 929-933 (1985).

"Delivering the Promise of Direct Beam Therapy"—Spectraprobe-PLR Catheter, 2 pages.

"Peripherals Are Our Business"—Laserguide, 2 pages.

Pankratov et al., "Instruments: A Step-Zoom Probe for Laser Endophotocoagulation: I. Design", Ophthalmic Surgery, vol. 18, No. 1, Jan. 1987, pp. 61-65.

Pankratov, "Algorithm for Calculating a Variable-Magnification Endophotocoagulation Probe", SPIE, vol. 713 Optical Fibers in Medicine II (1986), pp. 22-27.

FIBER OPTIC APPARATUS FOR USE WITH MEDICAL LASERS

This application is a continuation of application Ser. No. 364,703, filed on Jun. 9, 1989, now abandoned.

BACKGROUND OF THE INVENTION

The present invention relates to an improved lens configuration and method of producing the same, which serves to focus laser radiation and to provide a beam having a waist of relatively small cross-section, and long length at a selected location More particularly, the invention relates to a method and apparatus for the removal, penetration or treatment of human tissue or other biotic or nonbiotic growth, deposit or obstruction on or within the human body with a laser apparatus.

The use of radiation from lasers in medical and dental procedures has become of increasing importance over the years, allowing for use in surgery and treatment in a variety of medical fields, including urology, orthology, gastrology, cardiology and ophthalmology. Wavelengths ranging from the far ultraviolet, through the visible spectrum, to the far infrared, have been utilized, depending on the application. Typically, the laser light is transmitted to a surgery or treatment site through optical waveguides. Lenses at the output end of the fiber may be used to increase the intensity of the laser radiation.

SUMMARY OF THE INVENTION

The present invention comprises an optical apparatus which, in the preferred embodiment, functions as a laser catheter. The optical apparatus includes a source of light which is relatively incoherent, having a coherence factor of no less than about 2.0. The light emitted by the source has a minimum waist and a minimum waist radius $r_w$. In the preferred embodiment, the source of light comprises a laser coupled to a multimode optical fiber, and the minimum waist radius is equal to the radius of the core of the optical fiber. A lens receives an input beam of light from the optical fiber and the input beam is intercepted by the lens at a beam intercept radius $r_L$. The front principal plane of the lens is spaced from the minimum waist of the input beam by a distance S. The beam intercept radius $r_L$, when divided by the minimum waist radius $r_w$, yields a factor R having a value which depends upon the radius of the optical fiber core, or more generally, the minimum input waist radius. The factor R is between 1.5 and a value X which is no greater than 4.0 divided by twice the input waist radius $r_w$ (in millimeters). The lens has a focal length F which is selected in accordance with the above-mentioned distance S between the minimum input waist and the front principal plane of the lens such that the ratio of the focal length to the distance S is between 0.25 and 0.95.

In the preferred embodiment, the laser catheter utilizes interchangeable accessories which include hollow tips of varying size. Such hollow tips may be used to tactually determine the cutting action of the output laser beam. In one embodiment, the hollow tip terminates at a location between the lens and the location of minimum waist radius of the output beam. In another embodiment, the hollow tip terminates substantially at the location of the minimum waist radius of the output beam. In yet another embodiment, the hollow tip terminates at a location distal to the location of minimum waist radius. Preferably, the hollow tip is conically shaped and has an opening at the distal end thereof which is greater than the beam cross-section at such opening.

In a further embodiment of the invention, the lens has a refracting surface disposed distally to the catheter tip assembly. The lens preferably has a diameter substantially equal to the outside diameter of the catheter tip assembly. Such a lens may be utilized in a medical procedure in which the focusing power of the lens is first utilized to treat tissue or other biotic material without touching the material, and then used to heat the tissue or other biotic material by placing a surface of the lens in contact with the material. Preferably, the focused beam has a focal range of at least 1 mm, and a minimum waist radius of no more than 0.25 mm, located at least 3 mm from the rear principal plane of the lens.

DETAILED DESCRIPTION OF THE PREFERRED EMBODIMENT

Figure 1:
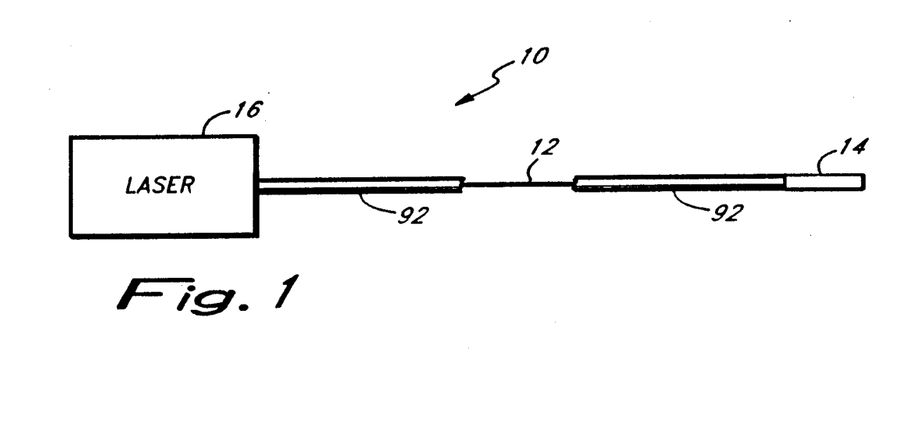
FIG. 1 is a schematic drawing illustrating the laser catheter connected to receive light from the laser source, and showing a portion of the catheter sleeve cut away to expose the optical fiber.

As shown in FIG. 1, a laser catheter 10 comprises a waveguide, such as an optical fiber 12, and a distal tip assembly 14. A light source, such as a laser 16, is coupled to supply light to the optical fiber 12. The wavelength of the light is selected to suit the particular medical application of interest and may be, for example, in the visible, ultraviolet or infrared wavelength ranges. The light passes through the fiber 12 and exits the catheter 10 at the distal tip assembly 14. As shown in FIGS. 2, 3, 4 and 5, the distal tip assembly 14 comprises a fiber holder sleeve 20, a lens mount sleeve 22, a fiber holder 24 (FIGS. 3 and 4) and a lens mount 26 (FIG. 3); each preferably comprised of a durable, heat-resistant and corrosion-resistant material. A brass alloy, half-hard, is contemplated for use in the structural components 20, 22, 24, 26, in combination with an outer protective plating comprising gold 15 millionths of an inch thick followed by a nickel strike 5 millionths of an inch thick.

Figures 2, 3, 4:
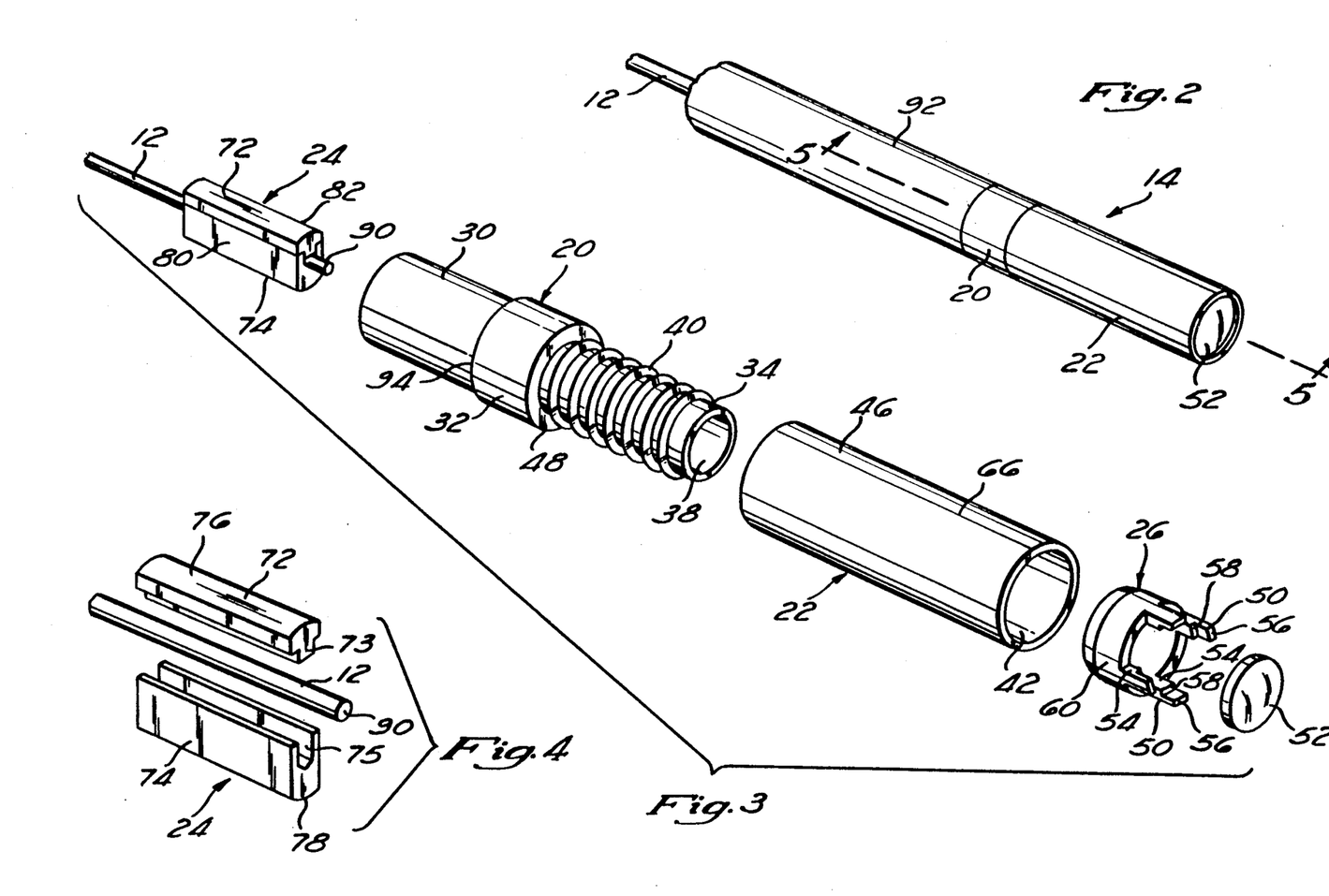
FIG. 2 is a perspective view of the apparatus of the present invention, showing the laser catheter tip and optical fiber.
FIG. 3 is a perspective view, in exploded form, of the component parts of the apparatus illustrated in FIG. 2.
FIG. 4 is an enlarged exploded view of the elongate optical fiber holder which retains the optical fiber.

The fiber holder sleeve 20 comprises a proximal sleeve portion 30, a central sleeve portion 32, and distal sleeve portion 34, as shown in FIG. 3. As used herein, the words proximal and distal are used in reference to proximity to the laser 16 which supplies the light to the fiber 12. The fiber holder sleeve 20 is cylindrical and has an axial bore 38 (FIG. 3) of uniform diameter throughout its length. The distal portion 34 of the fiber sleeve 20 has a reduced wall thickness relative to the central portion 32 so as to provide a reduced outside diameter. Threads 40 are disposed on the exterior surface thereof.

Figures 5, 6, 7:
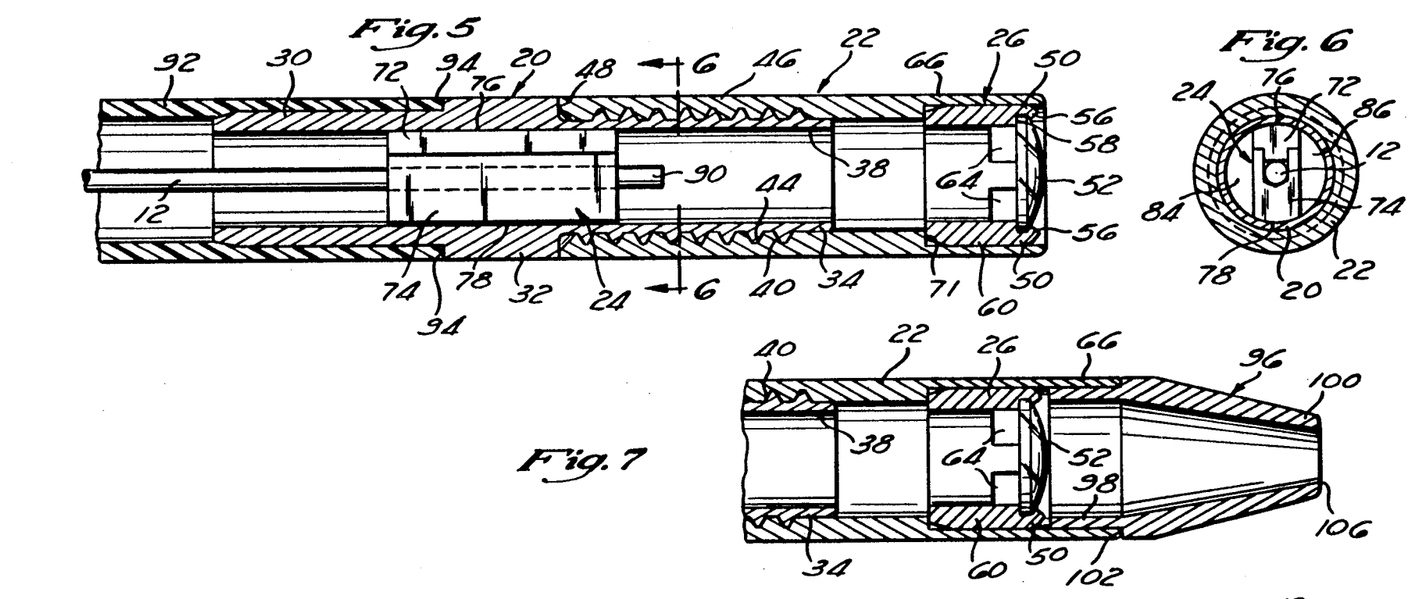
FIG. 5 is an enlarged, cross-sectional view of the laser catheter tip, taken along the lines 5—5 of FIG. 2.
FIG. 6 is a cross-sectional view taken along lines 6—6 of FIG. 5, showing the optical fiber holder mounted inside the fiber holder sleeve.
FIG. 7 is a cross-sectional view of the distal end of the laser catheter tip, showing an alternative embodiment wherein the distal end of the laser catheter tip has a conical sheath thereon.

The lens mount sleeve 22 is cylindrical and has a uniform diameter bore 42 (FIG. 3) therethrough. As shown in FIG. 5, female threads 44 are included at a proximal end portion 46 of the lens sleeve for mating with the male threads 40 on the distal sleeve portion 34 of the fiber holder sleeve 20. The lens sleeve 22 is secured to the fiber holder sleeve 20 by screwing the male threads 40 of the fiber holder sleeve 20 into the female threads 44 until the proximal end portion 46 of the lens sleeve 22 abuts shoulder 48 on the central portion 32 of the sleeve 20. A water-tight seal between the lens sleeve 22 and fiber holder sleeve 20 may be provided by the use of an appropriate washer, gasket or sealant compound. The outside diameters of the lens sleeve 22 and the central sleeve portion 32 of the fiber holder sleeve 20 are identical at their interface so as to avoid exterior surface irregularities in the catheter tip assembly 14.

The lens mount 26 comprises a cylindrical sleeve having a plurality of tines 50 disposed around its periphery at the distal end thereof. These tines 50 serve to grip and hold a lens 52 within the lens mount 26. Each of the tines 50 comprises a spacer portion 54 and a retainer portion 56. The lens 52 fits within the tines 50 of the lens mount 26 with the peripheral edge portion of the input side of the lens 52 resting on shoulders 58 of the spacer portions 54. The retainer portions 56 of the tines 50 are slightly peened over the peripheral edge portion of the lens 52 to hold the lens 52 in place without blocking the laser light exiting the lens 52. The spacer portions 54 of the tines 50 space the lens 52 from a main body 60 of the lens mount 26 so as to provide lateral openings 64 (FIG. 5) for fluid flow. The main body 60 of the lens mount 26 is sized to slide into a distal end portion 66 of the lens sleeve 22. The distal end portion 66 has a reduced wall thickness relative to the proximal end portion 46 of the lens sleeve 22, so as to provide an increased inside diameter for receiving the lens mount 26. The sleeve 22 includes a shoulder 71 (FIG. 5) which abuts the proximal end of the main body of the lens mount 26. The inside diameter of the lens mount 26 is the same as the inside diameter of the fiber holder sleeve 20. The diameter of the lens 52 is about midway between the inside diameter of the distal end portion 66 of the lens sleeve 22 and the inside diameter of the lens mount 26, so as to provide a fluid flow opening between the peripheral edge of the lens 52 and the distal end 66 of the lens sleeve 22. Due to the presence of the tines 50, this opening is in the form of a segmented annulus. The lens mount 26 is held within the distal end portion 66 of the lens sleeve 22 in a friction fit, preferably in combination with a heat and liquid resistant adhesive, such as cyanoacrylate.

The lens 52 of the preferred embodiment is a planoconvex spherical lens comprised of sapphire with the C-axis of the sapphire aligned with the optical axis of the lens 52. Sapphire has been found to be advantageous for reducing spherical abberation. The diameter of the lens is selected in accordance with the characteristics of the optical fiber, as discussed in detail hereinafter. However, a preferred maximum diameter is about 4 mm. Other embodiments have maximum lens diameters of 2.7 mm and 2.2 mm, respectively. In the preferred embodiment, the lens diameter is 1.3 mm.

The fiber holder 24 comprises an elongate member 72 having a T-shaped cross section and an elongate member 74 having a U-shaped cross section The member 72 has a channel 75 with a width approximately equal to that of the optical fiber 12. As shown in FIG. 4, the members 72, 74 are configured such that a central leg 73 of the T-shaped top member 72 fits snugly into the channel 75 formed in the U-shaped bottom member 74. The length of the central leg 73 is less than the depth of the channel 75 by an amount equal to the diameter of the optical fiber 12, so as to provide an elongate opening in which the optical fiber 12 is disposed. The optical fiber 12 is retained between the members 72, 74 by an interference fit or, alternatively, by chemical adhesive As shown in FIGS. 4, 5 and 6, the fiber holder 24 has opposing top and bottom surfaces 76, 78 on the members 72, 74, respectively, which have a curvature corresponding to the curvature of the axial bore 38 of the fiber holder sleeve 20. The members 72, 74 of the fiber holder 24 are sized for insertion into the bore 38 of the sleeve 20, such that the distance between the curved outer surfaces 76, 78 is approximately equal to the diameter of the bore 38, thereby permitting the fiber holder 24 to fit snugly in the sleeve 20. Preferably, the fiber holder is affixed to the sleeve 20 by a chemical adhesive. The distance between opposing side surfaces 80, 82 (FIG. 3) of the fiber holder 24 is significantly less than the diameter of the bore 38 to provide side channels 84, 86 (FIG. 6) for passage of fluid around the fiber holder 24. The fiber holder 24 retains the fiber 12 in an axial orientation such that the fiber axis is aligned with the central axis of the sleeves 20, 22. Preferably, the distal end 90 of the fiber 12 protrudes only a very small amount past the fiber holder to prevent sagging or bending of the end 90. The orientation of the fiber holder 24 within the fiber holder sleeve 20 is such that the optical fiber 12 placed therein is centered and axially aligned with the optical axis of the lens 52. The fiber 12 is held stationary within the fiber sleeve 20 so that the distance between the lens 52 and the distal end 90 of the fiber 12 remains constant. However, the relative position of the fiber end 90 and lens 52 can be adjusted by repositioning the fiber holder 24 within the fiber holder sleeve 20.

The optical fiber 12 is a multi-mode fiber comprising a core of relatively high refractive index which is surrounded by a cladding of relatively low refractive index. The core can be made of pure silica which has been fused, and the cladding which surrounds the core may comprise fused silica which has been doped to lower the refractive index The core material is preferably significantly free of metallic impurities, resulting in less attenuation of the transmitted laser energy as it travels through the fiber 12. Specific purpose fibers, which are readily available and known in the art, may be desirable for certain wavelengths which are difficult to transmit through optical fibers For example, UV grade fibers may be appropriate for very short wavelengths and zirconium fluoride fibers have been found to be advantageous for very long wavelengths Further, hollow core waveguides have found application in some cases.

The length of the fiber 12 is typically about 50 to 500 cm, and preferably about 200 to 400 cm. In one embodiment, the core has a diameter of approximately 200 microns, with a core plus cladding diameter of approximately 220 microns, and a numerical aperture of 0.22. Fiber core diameters for medical applications are typically in the range from 100 to 700 microns The optical fiber 12 is surrounded by a protective catheter sleeve 92 comprised of materials, such as PVC, cured epoxy or Teflon ®. The catheter sleeve 92 has an outside diameter which is equal to that of the central portion 32 of the fiber holder sleeve 24. In the preferred embodiment, the catheter diameter is 1.8 mm, although other embodiments have catheter diameters of 2.2 mm and 2.7 mm. In general, the diameter of the catheter sleeve 92 will typically be no more than 4.0 mm. The proximal portion 30 of the fiber holder sleeve 20 has an outside diameter which is reduced relative to the central portion 32 by twice the thickness of the catheter sleeve 92 to allow the catheter sleeve 92 to snugly fit over the portion 30, with the distal end of the catheter sleeve 92 abutting a shoulder 94 (FIG. 5) on the central portion 32 of the fiber holder sleeve 20. This permits the outer surface of the catheter sleeve 92 to blend smoothly into the outer surface of the catheter tip assembly 14 without surface irregularities. Preferably, the catheter sleeve 92 is affixed to the portion 30 by chemical adhesive to insure a water-tight connection.

A saline solution or gas stream from a pressurized source may be directed through the catheter sleeve 92 to the distal tip assembly 14 of the catheter 10. The saline solution or gas stream passes through the lateral openings 64 formed in the lens mount, exiting the catheter tip assembly between the periphery of the lens 52 and the lens sleeve 22. A vacuum system (not shown) may be associated with the laser catheter to collect ejected gas or saline from the catheter tip 14. The gas or saline may be advantageously used to reduce degradation of the lens 52. For example, when tissue is ablated by high peak energy laser light during an invasive surgical procedure such as cardiac angioplasty, the ablated products can sputter back towards the tip assembly 14 and deposit onto the lens 52. Such deposits on the lens 52 tend to absorb laser light and thereby produce thermal gradients which may crack or degrade the lens 52. Interposing a continuous layer of saline solution or gas between the lens 52 and the tissue inhibits debris from settling on the lens 52. In addition, the gas or saline solution may also be used to cool the lens 52 and fiber 12.

Referring to FIG. 7, an alternate embodiment of the laser catheter tip assembly 20 is shown. In this embodiment, distal portion 66 of the lens sleeve 22 is extended distally so as to provide a sleeve portion for the insertion of an accessory such as a hollow tactile tip which, in the preferred embodiment, comprises a conical sheath 96. The sheath 96 comprises a proximal end portion 98 and a distal end portion 100. The proximal end portion 98 is cylindrical and is sized for insertion into the extended distal end 66 of the lens sleeve 22 In the preferred embodiment, the proximal end portion 98 is bonded to the lens sleeve 22. The distal end portion 100 is conical in shape and has a diameter larger than the proximal end portion 98 at the juncture therebetween so as to provide an annular shoulder 102 which abuts the distal end 66 of the lens sleeve 22. A truncated tip 106 of the distal end 100 of the conical sheath 96 has an inner diameter at least as large as the diameter of the focused laser beam at its $1/e^2$ profile, thereby avoiding aperturing of the transmitted power of the laser beam passing therethrough. The $1/e^2$ beam profile will be understood by those skilled in the art as representing the portion of the beam which encircles about 85% of the beam intensity. A variety of axial lengths for the sheath 96 are contemplated, with the choice of length dependent upon the lens configuration used and the surgical result desired.

Figure 8:
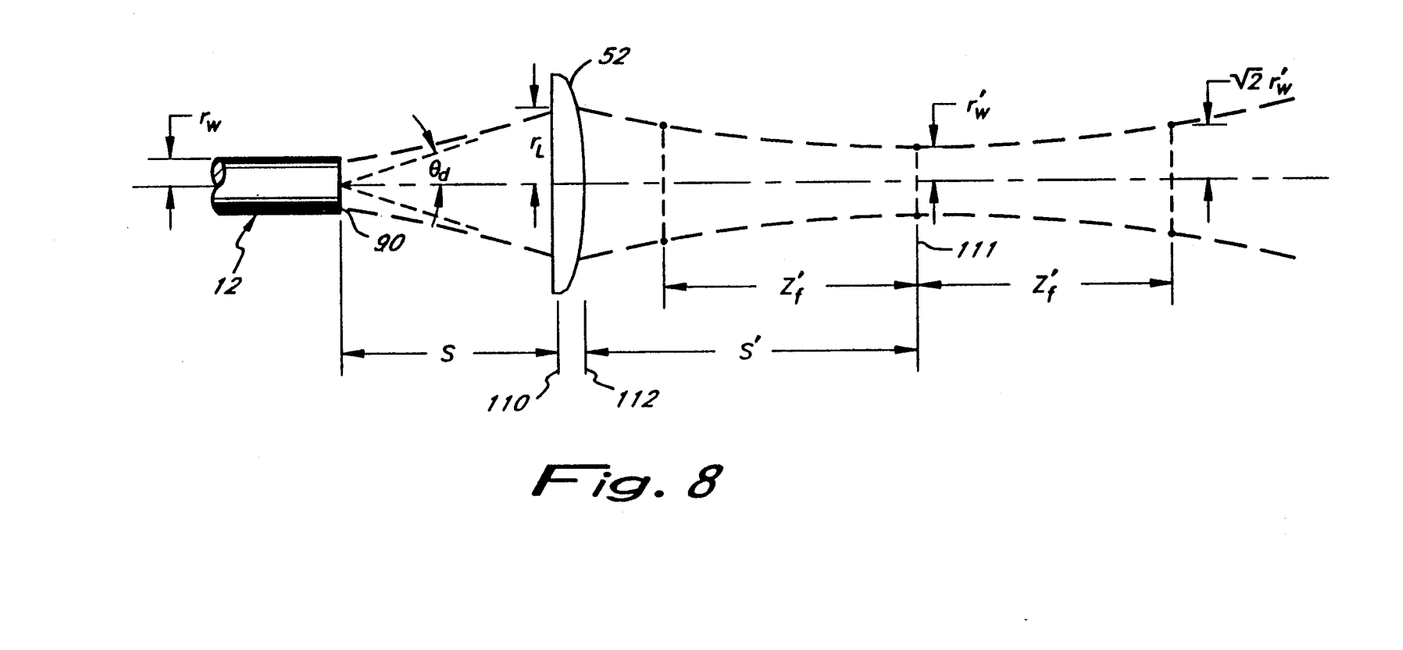
FIG. 8 is a schematic drawing showing the lens focusing the input beam to provide an output beam.

FIG. 8 shows a schematic drawing of the lens arrangement of the preferred embodiment As indicated therein by heavy dashed lines (representing the $1/e^2$ beam profile), light exiting the fiber 12 forms an input beam which is directed towards the lens 52. The input beam is focused by the lens 52 to provide an output beam.

The dimension labelled $r_w$ designates the minimum waist radius (i.e., the radius at the location of minimum cross-section) of the input beam for a finite area source. In the case of the preferred embodiment, the end 90 of the optical fiber 12 serves as the finite area source and the minimum input waist radius is the radius of the core of the optical fiber 12. Light from the optical fiber end 90 diverges at a finite angle $\theta_d$, commonly referred to as the divergence angle. This angle $\theta_d$ is related to the numerical aperture (NA) of the optical fiber by the following equation:

$$NA = \sin \theta_d \tag{1}$$

The numerical aperture (NA) is defined by the following relationship:

$$NA = \frac{\sqrt{n_{core}^2 - n_{clad}^2}}{n_{medium}} \tag{2}$$

where $n_{core}$ is the refractive index of the fiber core; $n_{clad}$ is the refractive index of the fiber cladding; and $n_{medium}$ is the refractive index of the surrounding medium From equation (2) it will be seen that the numerical aperture NA depends not only on fiber parameters, but also on the refractive index of the medium surrounding the fiber. Thus, in calculating the numerical aperture, attention must be given to factors such as whether the device will be used in conjunction with saline or used in air).

The optical fiber end 90 is spaced from the front principal plane 110 of the lens 52 by a distance S. In more general terms, the distance S represents the axial distance from the front principal 110 plane of the lens to the location 90 of the minimum input waist For lens systems employing multiple lens elements, any references herein to principal planes of the lens will be understood as referring to the principal planes of the lens system.

The numerical aperture (NA) and the distance S are preferably selected such that the light beam incident on the lens 52 has a radius $r_L$ at the $1/e^2$ beam profile. The dimension $r_L$ is referred to herein as the "beam intercept radius," which corresponds to the beam radius at the $1/e^2$ beam profile where the beam intercepts the front principal plane 110 of the lens (or, in the case of a multiple element lens system, the front principal plane of the lens system). In the preferred embodiment, the beam intercept radius is slightly less than the radius of the lens 52, and is equal to the radius of the lens 52 less the thickness of the peripheral edge of the lens 52 that is covered by the lens mount 24. For example, the tines 50 cover about 0.1 mm of the periphery of the lens 52. Thus, the 1.3 mm diameter (0.65 mm radius) lens 52 has a beam intercept radius of about 0.55. Mathematically, the beam intercept radius $r_L$ may be expressed as follows:

$$r_L = r_w \sqrt{1 + (S/Z_f)^2} \qquad (3)$$

where $Z_f$ is equal to $r_w/\sin \theta_d$. The parameter $Z_f$, referred to herein as the input focal range, represents the distance over which the input beam radius becomes $\sqrt{2}$ than the minimum waist radius of the input beam at the $1/e^2$ beam profile. Equation (3) may be rewritten as:

$$r_L = \sqrt{r_q^2 + (S \sin \theta_d)^2} \qquad (4)$$

where $\sin \theta_d = NA$ from equation (1).

The lens 52 has a focal length (F) which depends on factors such as the refractive index of the lens material, the refractive index of the surrounding medium and the curvature of the lens, as is well known in the art. A general formula for focal length is as follows $$\frac{1}{F} = (N-1)\left[C_1 - C_2 + \frac{T(N-1)}{N} C_1 C_2\right] \qquad (5)$$

where T is the thickness of the lens at its optical axis; $C_1$ is the curvature of the input side of the lens; $C_2$ is the curvature of the output side of the lens (note that $C_2$ is negative for a lens with a positive focal length); and N is the refractive index of the lens medium divided by the refractive index of the surrounding medium.

For a plano-convex lens, as utilized in the preferred embodiment, $C_1$ is zero, and equation reduces to:

$$\frac{1}{F} = (N-1)(-C_2) \qquad (6)$$

Corresponding equations for more complex lens designs are well known in the art and are available in the applicable literature. For a multiple element lens system, the focal length (F) is equal to the equivalent focal length of the lens system.

From the above equations, it will be seen that the focal length is dependent upon the medium which surrounds the lens, and thus, the focal length should be selected in accordance with the environment in which the lens is to be used. For example, if the lens is to be immersed in a saline solution during use, the focal length should be selected, taking into account the refractive index of the saline solution Similarly, if the lens is to be used in air, the focal length should take into account the refractive index of air (1.0).

The light passing through the lens 52 is focused by the lens 52 to form an output waist having a center 111 at which the beam waist is a minimum The $1/e^2$ radius of the beam waist at its center 111 is designated in FIG. 8 as the dimension $r'_w$. At an axial dimension $Z'_f$ on either side of the center 111 of the beam waist, referred to herein as the focal range of the output beam, the beam will have a radius of $\sqrt{2}\, r'_w$ at the $1/e^2$ profile, and the beam intensity will have dropped to one-half that at the center 111 of the beam waist The distance from the center 111 of the output beam waist (i.e., the location of minimum beam diameter) to the rear principal plane 112 of the lens is designated in FIG. 8 as the dimension S'. For the plano-convex lens 52 of the preferred embodiment, the rear principal plane 112 lies along a line tangent to the output face and perpendicular to the optical axis.

The lens arrangement of the present invention is specifically designed for use with relatively incoherent light having a coherence factor $K_c \geq 2$ and preferably $\geq 3$, where the coherence factor $K_c$ is defined as:

$$K_c = \frac{\pi r_w \theta_d}{\lambda} \qquad (7)$$

where $\lambda$ is the wavelength of the light and $r_w$ and $\theta_d$ are as defined above. Note that equation (7) may be applied to optical fibers through appropriate substitution of equation (1).

Those skilled in the art will understand that the coherence of the light passing through the lens depends on the coherence of the light emitted by the laser, and if an optical fiber is used, the properties of the optical fiber. Commercially available medical lasers commonly operate in multiple oscillating modes and produce relatively incoherent light. Multimode optical fibers, such as used in the preferred embodiment, typically propagate light in thousands of modes which are dispersive and which may mix the light as it propagates through the fiber. Such dispersion and mixing further reduce the coherence of the light, and, in general, the light in the fiber will be more incoherent when it leaves the fiber than when it entered.

For many medical applications, it is preferable to select a fiber and lens arrangement which yields (i) a relatively high intensity (small $r'_w$) at the center of the waist, (ii) a distance S' from the lens to the center of the waist which is relatively long, so as to provide a relatively long "throw" for the output beam, and (iii) a waist focal range $Z'_f$ which is relatively long. Unfortunately, these output beam characteristics relate to the lens system characteristics in a very complex and highly nonlinear way, which yields anomalies in the behavior of the output beam. For example, one of the more striking aspects of such anomalous behavior is that the throw of the output beam does not continuously increase as the distance S increases. It has been found that the location of the output waist will initially increase as S is increased and then suddenly reverse direction so as to move closer to the lens with increasing S. This behavior is quite surprising and is attributed to optical interactions associated with the incoherence of the beam. Further, as the distance S increases, the size of the minimum output waist decreases nonlinearly with respect to the minimum input waist. These anomalies and nonlinear behavior yield competing considerations which make it difficult to optimize the system parameters. By means of a unique and novel process, however, it has been discovered that the output beam parameters can, in general, be optimized by properly selecting the fiber and lens and positioning these elements relative to each other such that they satisfy the following relationships (8) and (9):

$$1.5 \leq R \leq X \qquad (8)$$

$$0.25 \leq F/S \leq 0.95 \qquad (9)$$

where (i) R is the ratio of the beam intercept radius ($r_L$) to the input waist radius $r_w$ (e.g., the radius of the fiber core), (ii) F and S are as defined above in reference to FIG. 8, and (iii) X is equal to the lens diameter divided by twice the input waist radius $r_w$.

In the preferred embodiment of the present invention, the maximum lens diameter is 4 mm, and thus, for an input beam minimum waist radius of 50 microns (corresponding to a fiber core diameter of 100 microns), the value of X in relationship (8) is 40, and the preferred range for R is 1.5 to 40. In general, the value of X and the associated range of appropriate values for R increases as the minimum waist radius decreases, and decreases as the minimum waist radius increases. By way of example, for an input beam minimum waist radius of 90 microns (corresponding to a fiber core diameter of 180 microns), the value of X is 22.2 and the range for R is 1.5 to 22.2; for an input beam minimum waist radius of 150 microns (corresponding to a fiber core diameter of 300 microns), the value of X is 13.3 and the range for R is 1.5 to 13.3; for an input beam minimum waist radius of 250 microns (corresponding to a fiber core diameter of 500 microns), the value of X is 8.0 and the range for R is 1.5 to 8.0, and, for an input beam minimum waist radius of 350 microns (corresponding to a fiber core diameter of 700 microns) the value of X is 5.7 and the range for R is 1.5 to 5.7.

In addition to the above described lens diameter, it has been found that the ranges given by relationships (8) and (9) are particularly appropriate for smaller lens diameters, e.g., 2.7 mm, 2.2 mm, and 1.8 mm or less.

Within the boundaries defined above for R and F/S, the lens and fiber parameters can be further refined to suit the particular medical application through an iterative process. In this process, the beam intercept radius $r_L$ and the fiber radius $r_w$ are selected to yield a value for R within the appropriate boundaries, as discussed above. The input beam focal range $Z_f$ is then determined by dividing the fiber radius by the numerical aperture of the fiber. The distance S is then determined in accordance with the following relationship:

$$S = Z_f \sqrt{R^2 - 1} \qquad (10)$$

For this distance S, a lens of appropriate focal length F is selected to satisfy relationship (9). The results are then applied to the following set of equations:

$$S'/F = 1 + \frac{S/F - 1}{(S/F - 1)^2 + (Z_f/F)^2} \qquad (11)$$

$$M = \frac{1}{[(1 - S/F)^2 + (Z_f/F)^2]^{\frac{1}{2}}} \qquad (12)$$

$$Z'_f = M^2 Z_f \qquad (13)$$

$$Z'_f = M^2 Z_f \qquad j(13)$$

where M is the magnification of the lens system (i.e., $r'_2$ divided by $r_w$).

Equations (11), (12) and (d13) can be solved to determine the characteristics of the output beam, namely, the magnification M (which determines $r'_w$), the distance S' between the lens and the center of the output waist and the focal range $Z'_f$ which is a measure of the length of the output waist.

The iterative process is repeated for various fibers and lenses until the desired lens arrangement for the particular application has been determined.

Relationships (8) and (9) thus provide a range of parameters which may be refined through use of equations (10)–(13). In general, however, it should be observed that use of an F/S value at the upper end of the range provides a relatively long beam throw with some sacrifice of intensity while an F/S value at the lower end of the range provides a relatively high beam intensity and a somewhat decreased beam throw. Lower R values tend to yield higher relative intensities (i.e., intensity of input beam minimum waist relative to output beam minimum waist) while higher R values tend to yield a longer beam throw, particularly at values of F/S near the upper end of the range. Further, for relatively large fiber diameters (>400 microns), it may be preferable to limit the value of F/S to 0.9 or less. In the preferred embodiment, the value of R is about 5.45 and the value of F/S is about 0.67.

Although the above equations were independently derived, it turns out that they have the same form as Self's Gaussian beam propagation equations. These equations are set forth in an article by Sidney A. Self entitled "Focusing of Spherical Gaussian Beams," Applied Optics, vol. 22, no. 5 (Mar. 1, 1983), which is incorporated herein by reference. Self's equations were derived for coherent light, while the equations (11), (12) and (13) were derived for incoherent light. The principal difference between Self's equations and equations (11), (12) and (13) above lies in the focal range parameter $Z_f$. In Self's equation, the rayleigh range $Z_r$ is used instead. While the parameters $Z_f$ and $Z_r$ occupy the same locations in the two respective sets of equations, they are calculated differently and yield quite different results.

As mentioned above, the parameter $Z_f$ is equal to $r_w/\sin \theta_d$. In contrast, Self's rayleigh range $Z_r$ is calculated as follows:

$$Z_r = \pi w_o^2/\lambda \qquad (14)$$

where $W_o$ is the minimum waist radius for the input beam and $\lambda$ is the optical wavelength.

The similarity in form between Self's Gaussian beam propagation equations and equations (11), (12) and (13) make it quite easy to perform the above-described iterative process on a computer. There are a number of commercially available computer programs suitable for solving Self's Gaussian beam propagation equations, such as the "Code 5" software by Optical Research Associates of Pasadena, Calif., which is incorporated by reference herein These computer programs may be adapted to solve equations (11), (12) and (13) by setting $w_o = r_w$ and $Z_r = Z_f$, and by entering the following wavelength $\lambda^*$ (referred to herein as the "fictitious wavelength") for $\lambda$:

$$\lambda^* = \pi r_w \theta_d \qquad (15)$$

Interestingly, the fictitious wavelength $\lambda^*$ can be quite long, and it has been found that the fictitious wavelength for some incoherent optical source arrangements extends into the microwave region.

While the above equations were derived as a Gaussian beam approximation for incoherent light, it has been found that the approximation is nearly as good for beams having a uniform distribution. Since the light output from multimode fibers typically has a generally uniform beam distribution, the equations can be applied quite advantageously to such fibers.

The output waist position, S', and the minimum output beam radius, $r'_w$, calculated from equations (11)–(13) assume that the focusing lens is free of aberration. In practice, however, lenses may exhibit certain aberrations such as spherical aberration, the amount of which can be determined according to well known techniques. For the simple plano-convex lens 52 of the preferred embodiment, the presence of aberrations (particularly spherical aberration) can result in output waist parameters somewhat different than those computed with the above equations. Nevertheless, the amount of the difference appears to be quite small. In a typical case involving a sapphire (the presently preferred material) plano-convex lens, the actual minimum waist position, S', was found to be only 16% shorter than the value found from equation (10). The value of the output waist radius, $r'_w$, was found to be essentially the same as that calculated with equation (11). Thus, in practice, aberrations do not have a major impact on the choice of an optimum lens design based on the equations presented above. Additionally, the effects of aberrations can be reduced or substantially eliminated by using a lens with an aspheric surface or by using a multi element spherical lens system, as is well known in the art. The above-described optical arrangements and techniques may be used to produce an output light beam having a relatively small beam waist at the point of minimum radius ($r'_w$), a relatively long beam "throw" (i.e., long distance S') and a relatively long focal range ($Z'_f$). The present invention preferably provides a beam throw (i.e., distance S') of approximately 3–6 mm. A typical beam throw for general use can be on the order of 4 mm. A relatively long throw distance is advantageous in that it places the focus away from the end of the catheter and allows the user to better observe the beam of area to be cut or treated. Further, a long throw tends to reduce backsplash of tissue particles onto the lens 52.

The focal range ($Z'_f$) on either side of the minimum waist location is preferably about 1–2 mm, with a typical distance of 1.5 mm. A relatively long focal range is desirable in that it provides a substantial distance through which the intensity of the beam waist is relatively high. Thus, the beam does not have to be as precisely positioned, and there is a degree of "play" on either side of the minimum waist so as to allow for greater control and "feel" for the procedure by the user of the laser catheter.

A small waist size is advantageous not only for increasing power density at the focus spot, but also for decreasing the power output requirements of the laser source 16. A reduction in the power requirements of the light source allows use of a laser which is less powerful and thereby more compact and portable than those conventionally used in medical applications. In general, the minimum waist diameter is preferably within the range of 0.1–0.4 mm, but for some applications a minimum waist diameter of about 0.25 mm or less is preferred.

A small waist diameter also permits a reduction in the maximum diameter of the catheter 10 as less transmitted light is needed to provide an equal or greater amount of cutting power at the desired focus compared to a conventional laser catheter apparatus. A reduced catheter diameter provides greater ease of access and positioning for the laser catheter apparatus into areas which may have been nonaccessible, or accessible with extreme difficulty or manipulation in a conventional laser catheter apparatus. For instance, in conventional orthoscopic surgery, the use of laser catheters on tears of the posterior medial meniscus of the knee presently require a manual or mechanical pulling of the femur away from the meniscus as to allow access of conventional laser catheters to repair the tear in the ligament or cartilage. A reduced diameter catheter will enhance the ease of catheter insertion between the femur and the meniscus without a manual manipulation of the knee and leg area of the patient, thereby reducing the risk of trauma, injury or pain to the patient, and, additionally, provide a more accurate and precise surgery. The long throw and focal range of the output laser beam is also beneficial in a variety of invasive medical applications in orthoscopic surgery in that the laser catheter tip 14 may be placed a significant distance away from the surgical or removal site to again lessen the chance of additional trauma or injury to the surgical patient, provide a greater control or "feel" for the user and allow for easier viewing of the site to be treated.

In the preferred embodiment, the fiber 12 has a core diameter of 200 microns, as mentioned above, and the numerical aperture of the fiber 12 is 0.22. The laser 16 is a Nd:YAG laser which, when used with the optical fiber 12, provides light at the fiber end 90 having a coherence factor on the order of about 65. The laser 16 of the preferred embodiment has a wavelength of 1.064 microns. The lens 52 is plano-convex, having a diameter of 1.3 mm, a beam intercept radius of 0.545 mm and a focal length of 1.7 mm. The thickness of the lens 52 (measured across the optical axis of the lens) is 0.315 mm, and the lens 52 is formed of sapphire with its C-axis aligned with the optical axis of the lens. The distance S between the lens 52 and the end 90 of the fiber 12 is about 2.53 mm, which yields a distance S' for the location of the minimum output waist of 4.45 mm. The factor R is about 5.45 and the ratio F/S is about 0.67. The beam cross-section diameter at the location of the minimum output waist is about 350 microns for the $1/e^2$ beam profile and the focal range $Z'_f$ is about 1.45 mm (or $2 Z'_f = 2.9$ mm). For the preferred embodiment, both the catheter tip assembly 14 and the catheter sleeve 92 have a diameter of 1.8 mm. The above-described arrangement provides 26 times more concentrated energy than the energy available 4.45 mm away from a bare (no lens) fiber.

Figure 9A:
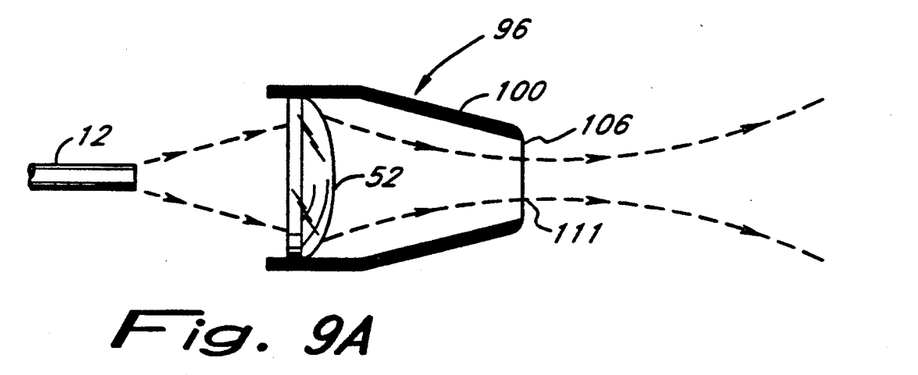
FIGS. 9A–9C illustrate three arrangements for sizing the conical sheath relative to the output beam.
Figure 9B:
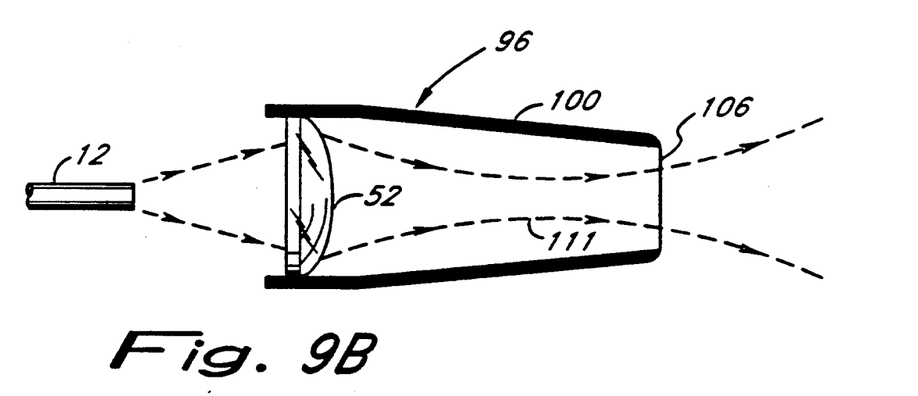
Figure 9C:
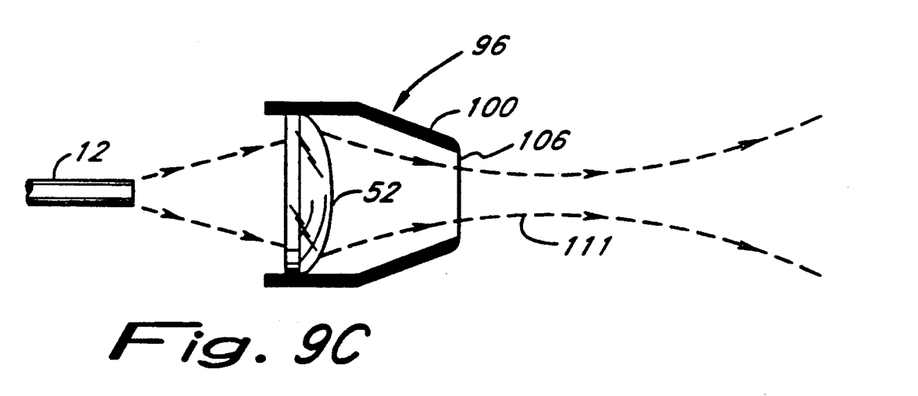

Referring to FIGS. 9A, 9B and 9C, three schematic drawings of the focused light pattern which emerges from the lens 52 are shown. The configuration of the sheath 96 may be selected in accordance with the focused light pattern to provide a tactile indicator as to the cutting action of the laser light exiting the catheter 10. For example, as shown in FIG. 9A, the conical sheath 96 attached to the distal end 66 of the lens sleeve 22 (FIG. 7) may be sized so that its truncated tip 106 terminates at the point 111 of minimum waist radius $r'_w$ of the focused output light beam. Since the region near the point of minimum waist radius $r'_w$ of the focused laser light provides maximum laser power per unit of area, sizing the conical sheath 96 such that the tip 106 of the distal end 100 of the conical sheath 96 terminates at the minimum waist radius of the beam allows the user to thereby tactually apply the tip 106 to the tissue for maximal laser cutting power.

FIG. 9B. depicts an alternate embodiment of the conical sheath 96, wherein the truncated tip 106 of the distal end 100 of the sheath 96 terminates beyond the point 111 of minimum waist radius $r'_w$ of the focused output light beam. Sizing the length of the sheath 96 so that the tip 106 extends distally beyond the point of minimum cross-section of the output beam assures that a surface abutting the tip 106 is exposed to defocused laser light. The defocused laser light permits cutting or treatment of a larger surface area.

FIG. 9C depicts another alternative embodiment of the conical sheath 96, wherein the truncated tip 106 terminates in front of the location 111 of minimum waist diameter $r'_w$ of the focused light. Such a positioning of the tip 106 provides a projected beam focus for relatively deep cutting or treatment beyond the end of the conical tip 106. In this configuration, the cutting becomes more aggressive with increasing tissue depth as the location where the minimum beam waist occurs is approached, and the user can tactually determine that the point of laser focus is beyond the area where the tip 106 of the sheath 96 is abutting.

The tapered conical configuration of the sheath 96 additionally acts as a funnel for flowing cooling gas, or saline solution, to the site of the laser-tissue interaction. As the inside diameter of the sheath 96 decreases, the velocity of exiting gas or liquid increases. This serves to reduce the amount of tissue, blood or particulate matter ejected back toward the lens 52 and depositing thereon, thereby enhancing performance of the catheter. In the preferred embodiments, the location 111 of minimum output waist radius is at least one focal range away from the rear principal plane of the lens and the tactile tip 96 terminates within one focal range of the location of minimum waist radius. Further, the location 111 of the minimum output waist radius is preferably at least one focal length from the rear principal plane of the lens 52.

Various combinations of lasers and hollow tips can be used without changing the catheter merely by unscrewing the lens sleeve 22 and replacing it with a lens sleeve having a different lens and hollow tip. Other types of accessories such as contact tips can be attached to the catheter in a similar manner, thereby allowing one laser catheter to be used for a variety of purposes. For instance, removal of a plaque deposit may be accomplished using one of the sheaths 96. Cauterization of a blood vessel during the cardiac laser angioplasty may be accomplished without changing the catheter, merely by replacing the sleeve 22 with an ordinary contact tip, or with a sleeve having a different sheath and lens.

Figure 10:
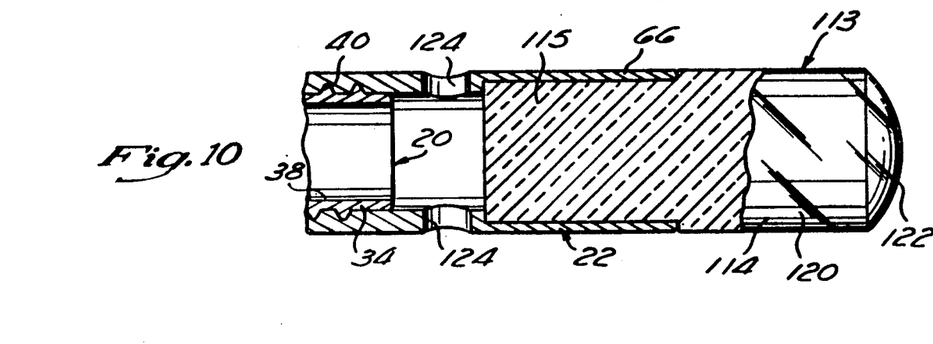
FIG. 10 is a cross-sectional view of an alternative embodiment of the catheter tip, wherein the lens extends beyond the end of the lens sleeve.

Referring to FIG. 10, an alternate embodiment of the laser catheter tip assembly 14 utilizes a thick lens 113 having a length which is substantially longer than its diameter. The lens 113 includes a proximal end 115 and a distal end 114. The proximal end 115 is cylindrical and sized for insertion into the opening 42 (FIG. 3) of the distal end 66 of the lens sleeve 22 so as to abut shoulder 71. The distal end 114 comprises an elongate cylindrical body portion 120 having a convex lens surface 122, which is disposed distally beyond the lens sleeve 22. The body portion 120 has a diameter which is at least as large as, but preferably equal to, that of the lens sleeve 22. Ejection holes 124 formed in the lens sleeve 22, between the lens 113 and fiber holder sleeve 20, provide openings to expel a cooling gas and/or saline solution. The thick lens 113 is advantageous in that it provides an increased beam intercept radius $r_L$ relative to that of the lens 52. By positioning the lens refracting surface 122 distally beyond the lens mounting sleeve 22, the lens refracting surface 122 can be larger than would be otherwise possible, since its diameter is not restricted by a surrounding lens mount. In the preferred embodiment, the diameter of the lens 113 at the refracting surface 122 is substantially equal to the maximum diameter of the catheter tip assembly 14. The larger refracting surface permits the lens 113 to focus the output beam more tightly than the lens 52 (other things being equal) and thus may be quite desirable for some applications. A further advantage of the lens 113 is that it may be used as a contact tip for cauterization. During use, the lens will typically be heated by the laser light to a temperature sufficient for cauterization, and the curved distally disposed lens refractive surface 122 can be used in the same manner as a contact tip, if desired. Thus, the lens could be initially used to cut tissue and then used to cauterize the same tissue, which thereby allows both procedures to be performed without the need to change catheters or even catheter tips. The lens 113, in the instant embodiment, is preferably comprised of sapphire.

It is to be understood that the constructions described and illustrated above represent only the presently preferred embodiments of the invention and that various modifications and additions may be made to those embodiments without departing from the scope and spirit of the present invention.

What is claimed is:

1. An apparatus, comprising:
    an optical waveguide for emitting light having a minimum waist and a minimum waist radius $r_w$, said light being relatively incoherent and having a coherence factor $K_c$ of no less than about 2.0; and
    a lens for focusing said light, said lens being of substantially uniform composition and having (i) a diameter of no more than 4 millimeters, (ii) a focal length F, (iii) a beam intercept radius $r_L$, and (iv) a front principal plane which is spaced from said minimum waist by a dimension S, said light source and said lens being positioned relative to each other to satisfy the relationships.

$$1.5 \leq R \leq X$$

and $$0.25 \leq F/S \leq 0.95$$

wherein R is equal to $r_L/r_w$, and X is no greater than 4 divided by twice the minimum waist radius $r_w$ in millimeters.

2. The apparatus of claim 1, wherein said lens of substantially uniform composition comprises sapphire.

3. The apparatus of claim 1, wherein said lens is plano-convex.

4. The apparatus of claim 1, wherein said lens comprises a single lens element.

5. The apparatus of claim 1, wherein said lens has an input surface and an output surface, and wherein said lens focuses said light to provide an output beam minimum waist radius located at least 2 mm from the output surface of said lens.

6. The apparatus of claim 1, wherein said lens focuses said light to provide an output focal range $Z'_f$ of at least 1 mm.

7. The apparatus of claim 1, wherein said lens focuses said light to a diameter of 0.1 to 0.4 mm.

8. The apparatus of claim 1, wherein said lens focuses said light to a diameter of less than 0.25 mm.

9. The apparatus of claim 1, wherein X is no greater than 2.7 divided by twice the minimum waist radius $r_w$ in millimeters.

10. The apparatus of claim 1, wherein said waveguide is secured to a distal tip assembly of a catheter, said tip assembly mounting said lens, said lens having a refracting surface disposed distally to said tip assembly and having a diameter substantially equal to the outside diameter of said tip assembly.

11. The apparatus of claim 1, wherein said beam intercept radius is less than the radius of said lens.

12. The apparatus of claim 1, wherein the value of F/S is no more than about 0.9 and the minimum waist radius is at least about 200 microns.

13. The apparatus of claim 1, additionally comprising a member for mounting said lens, said lens mounting member having an opening for mounting said lens, said lens having (i) an input surface, and (ii) an output surface comprising a refracting surface configured to refract light, said refracting surface being larger than said opening, said waveguide being positioned relative to said lens to (i) illuminate said input surface with a beam having a radius less than the radius of said opening, and (ii) illuminate said refracting surface with a beam having a radius greater than the radius of said opening.

14. The apparatus of claim 13, wherein said refracting surface is distally spaced from said mounting member.

15. The apparatus of claim 1, additionally comprising a flexible catheter tube for delivering a fluid to a treatment site, said waveguide being disposed within said tube.

16. The apparatus of claim 15, wherein said catheter tube has a diameter of no more than about 4 mm.

17. The apparatus of claim 1, wherein said waveguide comprises a multimode optical fiber having a core diameter of at least about 100 microns but no more than about 700 microns.

18. The apparatus of claim 17, wherein said core of said optical fiber is comprised of fused silica.

19. The apparatus of claim 1, wherein said optical waveguide is coupled to a laser and wherein said minimum waist is at the output end of said waveguide.

20. The apparatus of claim 19, wherein said laser produces light outside a visible range of the optical spectrum.

21. The apparatus of claim 20, wherein said light is in the infrared region of the optical spectrum.

22. The apparatus of claim 1, wherein said waveguide comprises an optical fiber, said fiber secured to a distal tip assembly of a catheter, said tip assembly comprising (i) an elongate fiber holder disposed within a fiber holder sleeve and (ii) a lens mount for mounting said lens.

23. The apparatus of claim 22, wherein said lens mount comprises plural tines for engaging a peripheral edge of said lens, said lens mount further including fluid flow openings between said tines.

24. The apparatus of claim 22, wherein said lens mount is secured to said fiber holder sleeve by a lens sleeve.

25. The apparatus of claim 24, wherein said fiber holder is comprised of a first member having a channel for receiving said fiber and a second member for holding said fiber within said channel.

26. The apparatus of claim 1, wherein said waveguide is secured to a distal tip assembly of a catheter, said tip assembly mounting said lens, said apparatus additionally comprising a hollow tip attached to said tip assembly.

27. The apparatus of claim 26, wherein said hollow tip comprises a conical sheath.

28. The apparatus of claim 26, wherein said hollow tip terminates at a location which is within one focal range $Z'_f$ of the location of minimum waist radius of the light focused by said lens.

29. The apparatus of claim 28, wherein said hollow tip terminates at a location between said lens and said location of minimum waist radius of the light focused by said lens.

30. The apparatus of claim 28, wherein said hollow tip terminates substantially at said location of minimum waist radius of the light focused by the lens.

31. The apparatus of claim 28, wherein said hollow tip terminates at a location distal to the location of minimum waist radius of the light focused by said lens.

32. An apparatus, comprising:
an optical waveguide for outputting a beam of light, said waveguide having a core radius, said light being relatively incoherent with a coherence factor of at least about 2.0, said beam having a minimum waist at the output end of said waveguide with a minimum waist radius $r_w$, said minimum waist radius being equal to the radius of the core of said waveguide; and
a lens for focusing said light, said lens being of substantially uniform composition and having (i) a diameter of no more than 2.2 millimeters, (ii) a focal length F, (iii) a beam intercept radius $r_L$, and (iv) a front principal plane which is spaced from said minimum waist by a dimension S, said waveguide and said lens being positioned relative to each other to satisfy the following relationships:

$$1.5 \leq R \leq X$$

and $$0.25 \leq F/S \leq 0.95$$

wherein R is equal to $r_L/r_w$, and x is equal to 2.2 divided by twice the core radius of said fiber in millimeters.

33. The apparatus of claim 32, wherein said lens is comprised of sapphire.

34. The apparatus of claim 32, wherein said lens is plano-convex.

35. The apparatus of claim 32, wherein said lens is comprised of a single element.

36. The apparatus of claim 32, wherein said waveguide is secured to a distal tip assembly of a catheter, said tip assembly mounting said lens, said lens having a refracting surface disposed distally to said tip assembly and having a diameter substantially equal to the outside diameter of said tip assembly.

37. The apparatus of claim 32, wherein said beam intercept radius is less than the radius of said lens.

38. The apparatus of claim 32, wherein said waveguide comprises an optical fiber of fused silica.

39. The apparatus of claim 32, additionally comprising a member having an opening for mounting said lens, said lens having (i) an input surface and (ii) an output surface comprising a refracting surface configured to refract light, said refracting surface being larger than said opening, said waveguide being positioned relative to said lens to (i) illuminate said input surface with a beam having a radius less than the radius of said opening, and (ii) illuminate said refracting surface with a beam having a radius greater than the radius of said opening.

40. The apparatus of claim 39, wherein said refracting surface is distally spaced from said mounting member.

41. The apparatus of claim 32, wherein said waveguide is coupled to a laser which produces light outside a visible range of the optical spectrum.

42. The apparatus of claim 41, wherein said light is in the infrared region of the optical spectrum.

43. The apparatus of claim 32, wherein said waveguide is secured to a distal tip assembly of a catheter, said apparatus additionally comprising a flexible catheter tube for delivering a fluid to said tip assembly, said waveguide being disposed within said tube.

44. The apparatus of claim 43, wherein said catheter tube has a diameter of no more than about 2.2 mm.

45. The apparatus of claim 32, wherein said waveguide is secured to a distal tip assembly of a catheter, said tip assembly mounting said lens, said apparatus additionally comprising a hollow tip attached to said tip assembly.

46. The apparatus of claim 45, wherein said hollow tip comprises a conical sheath.

47. The application of claim 45, wherein said hollow tip terminates at a location which is within one focal range $Z'_f$ of a location of minimum waist radius of the light focused by said lens.

48. The apparatus of claim 47, wherein said hollow tip terminates at a location between said lens and said location of minimum waist radius of the light focused by said lens.

49. The apparatus of claim 47, wherein said hollow tip terminates substantially at said location of minimum waist radius of the light focused by the lens.

50. The apparatus of claim 47, wherein said hollow tip terminates at a location distal to the location of minimum waist radius of the light focused by said lens.

51. The apparatus of claim 41, wherein said laser comprises an Nd:YAG laser.

52. An apparatus, comprising:
   an optical waveguide for transmitting light;
   a lens having a focal length F for focusing said light on a treatment site, said lens having a diameter of no more than 4 mm and being of a substantially uniform composition;
   a distal tip assembly secured to said optical waveguide, said tip assembly mounting said lens a distance S from an end of said waveguide, the ratio of F/S being between 0.25 and 0.95, the focused light having a location of minimum waist radius and a focal range, said location of minimum waist radius being greater than one focal range $Z'_f$ from the rear principal plane of said lens; and
   a hollow tip adapted for attachment to said distal tip assembly, said hollow tip (i) terminating at a location which is in proximity to said location of minimum waist radius of said focused light, and (ii) having an opening at the distal end thereof which is approximately equal to or greater than the $1e/^2$ beam profile at said opening.

53. The apparatus of claim 52, wherein said hollow tip terminates at a location between said lens and said location of minimum waist radius of the light focused by said lens.

54. The apparatus of claim 52, wherein said hollow tip terminates substantially at said location of minimum waist radius of the light focused by the lens.

55. The apparatus of claim 52, wherein said hollow tip terminates at a location distal to the location of minimum waist radius of the light focused by said lens.

56. The apparatus of claim 52, wherein said hollow tip is conically shaped.

57. The apparatus of claim 52, wherein said location of said minimum waist radius is at least about 3 mm from the rear principal plane of said lens and wherein said focal range is at least about 1.5 mm.

58. The apparatus of claim 52, wherein said location at which said tip terminates is within one focal range $Z'_f$ of the location of said minimum waist radius.

* * * * *

UNITED STATES PATENT AND TRADEMARK OFFICE
CERTIFICATE OF CORRECTION

PATENT NO. : 5,207,673
DATED : May 4, 1993
INVENTOR(S) : Wendell V. Ebling, et al It is certified that error appears in the above-indentified patent and that said Letters Patent is hereby corrected as shown below:

Column 18, line 19, claim 52, line 20, change "1e/$^2$" to --1/$e^2$--.

Signed and Sealed this

First Day of March, 1994

Attest:

Attesting Officer

BRUCE LEHMAN

Commissioner of Patents and Trademarks